US011253697B2

(12) United States Patent
Su

(10) Patent No.: US 11,253,697 B2
(45) Date of Patent: Feb. 22, 2022

(54) IMPLANTABLE CUFF WITH AN INTEGRAL CLOSURE MECHANISM

(71) Applicant: Ning Miao Su, Irvine, CA (US)

(72) Inventor: Ning Miao Su, Irvine, CA (US)

(73) Assignee: NING MIAO SU

( * ) Notice: Subject to any disclaimer, the term of this patent is extended or adjusted under 35 U.S.C. 154(b) by 159 days.

(21) Appl. No.: 16/139,083

(22) Filed: Sep. 23, 2018

(65) Prior Publication Data

US 2020/0094050 A1  Mar. 26, 2020

(51) Int. Cl.
| *A61N 1/05* | (2006.01) |
| *A61M 37/00* | (2006.01) |
| *A61B 17/12* | (2006.01) |
| *A61B 5/24* | (2021.01) |
| *A61B 17/00* | (2006.01) |

(52) U.S. Cl.
CPC .............. *A61N 1/0556* (2013.01); *A61B 5/24* (2021.01); *A61B 17/12013* (2013.01); *A61M 37/00* (2013.01); *A61B 2017/00477* (2013.01)

(58) Field of Classification Search
CPC .. A61N 1/0556; A61M 37/00; A61B 5/04001; A61B 17/12013; A61B 2017/00477
See application file for complete search history.

(56) References Cited

U.S. PATENT DOCUMENTS

| 3,379,218 A | * | 4/1968 | Conde | B29C 61/10 138/99 |
| 3,495,306 A | * | 2/1970 | Eichberg | A44B 19/16 24/586.1 |
| 3,517,702 A | * | 6/1970 | Trimble | H02G 3/0481 138/128 |
| 3,654,049 A | * | 4/1972 | Ausnit | A44B 19/16 24/16 PB |
| 3,682,163 A | * | 8/1972 | Plummer | A61F 5/05858 602/6 |
| 3,765,329 A | * | 10/1973 | Kirkpatrick | B26D 7/20 101/415.1 |
| 3,846,575 A | * | 11/1974 | Troy | H02G 3/0481 174/41 |
| 4,268,559 A | * | 5/1981 | Smuckler | B29C 61/10 428/99 |
| 4,378,393 A | * | 3/1983 | Smuckler | B29C 61/10 428/99 |

(Continued)

*Primary Examiner* — Amy R Weisberg

(57) ABSTRACT

An integral closure mechanism is described to be used for implantable cuffs of tubular shapes. This mechanism relates to cuffs used to surround internal organ or tissue in animals and human for specific clinical applications or for evaluation purposes in biomedical research. The closure mechanism is designed to provide a safe and reliable way in keeping the cuff in its original dimension around biological tissue, and to assist in surgical implantation by introducing a convenient and less time-consuming method to secure the cuff at the surgical site. To eliminate distortion of the implantable cuff by having an integral closure mechanism, the underlying body tissue is better protected from damages caused by compression of the cuff and from connective tissue over-growing at the distorted sites. Thus, therapeutic attempts by using implantable cuffs may reach their desired potential in various applications.

21 Claims, 7 Drawing Sheets

1. Tubular cuff membrane
2. Closure mechanism
3. Lumen

(56) References Cited

U.S. PATENT DOCUMENTS

| | | | | | |
|---|---|---|---|---|---|
| 4,388,488 A * | 6/1983 | Wlcek | H02G 15/1813 174/92 |
| 4,442,153 A * | 4/1984 | Meltsch | H02G 15/1813 428/99 |
| 4,463,046 A * | 7/1984 | Hutchison | B29C 53/06 428/126 |
| 4,478,381 A * | 10/1984 | Pittion | F16L 3/1075 248/71 |
| 4,714,277 A * | 12/1987 | Bachel | B29C 61/10 174/DIG. 8 |
| 4,858,286 A * | 8/1989 | Siegel | A44B 19/16 24/585.12 |
| 4,865,890 A * | 9/1989 | Erlichman | B29C 61/10 428/35.1 |
| 4,898,492 A * | 2/1990 | Janowski | A44B 19/34 24/584.1 |
| 4,939,819 A * | 7/1990 | Moyer | H02G 3/0481 24/16 R |
| 4,944,976 A * | 7/1990 | Plummer, III | H02G 3/0481 138/110 |
| 5,129,608 A * | 7/1992 | Goldman | B29C 61/0608 248/74.3 |
| 5,217,001 A * | 6/1993 | Nakao | A61B 1/00135 24/DIG. 50 |
| 5,487,756 A * | 1/1996 | Kallesoe | A61N 1/0556 600/381 |
| 5,987,706 A * | 11/1999 | Boe | B65D 63/1018 24/16 PB |
| 6,461,368 B2 * | 10/2002 | Fogarty | A61B 17/02 264/243 |
| 6,712,755 B2 * | 3/2004 | Chang | A61B 1/00142 600/114 |
| 2012/0197371 A1 * | 8/2012 | Neisz | A61N 1/0556 607/118 |

\* cited by examiner

1. Tubular cuff membrane
2. Closure mechanism
3. Lumen

A. near circumferential cuff membrane
B. semi-flexible hinge
C. closure mechanism
D. one locking unit FIG. 3A  Implantable cuff cross sectional view at the closed position FIG. 3B  Implantable cuff cross sectional view at the opened position 1. Closing component A along one edge of the tubular cuff
2. Closing component B along the other edge of the tubular cuff
3. One locking unit C

H. Holding Points
P. Pressing Points
U. semi-flexible hinge

Fig. 6A  enclosing a nerve with the implantable cuff
  N: Nerve    F: Fascicle

Fig. 6B  implantable cuff enclosed a nerve

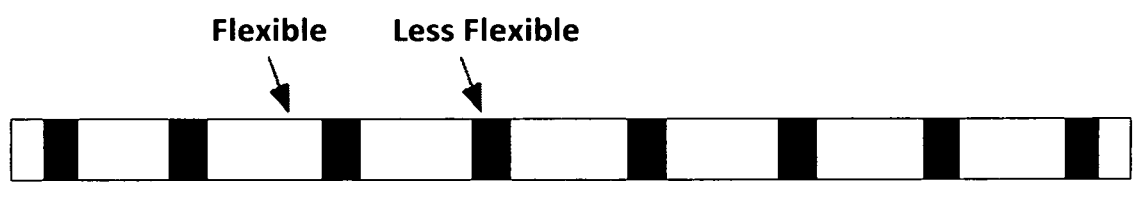
FIG. 7 semi-flexible hinge side view

US 11,253,697 B2

IMPLANTABLE CUFF WITH AN INTEGRAL CLOSURE MECHANISM

FIELD OF THE INVENTION

This mechanism is designed for implantable cuffs used in both fields of research and clinical settings. The intended applications of cuffs or a particular study of interest do not relate to this mechanism. Biomedical research, animal studies, clinical applications for treatments at the hospital, or localized pharmacological approach are potential fields to receive benefits of using implantable cuffs with this mechanism. This closure mechanism is incorporated to be part of the implantable cuff to give a better seal along the edges of the cuff, and to stabilize cuffs with locking units to avoid unwanted re-opening of cuffs during implantation and after completion of the surgical procedure.

BACKGROUND OF THE INVENTION

Several implantable cuffs have been used in research and very few are used in clinical settings for treatments. Prior cuffs were designed to enclose the tissue and to close with sutures. There are disadvantages from the use of sutures to close the cuff. For instance, suture material either absorbable or non-absorbable can retain contaminants or serve as a focal point for connective tissue to grow around it. Sutures used for implantation has a lifetime of a few months inside a human body to provide a constant tensile strength. Sutures may be required to close the cuffs for an extended period-of-time to prevent re-opening of the cuffs for the clinical applications. Another disadvantage is when sutures do not close the cuff tightly, connective tissue may grow inside the cuff, and this interferes with the interaction at the interface between the cuff and the enclosed tissue. When sutures close the cuff too tightly, it may lead to inflammation at the enclosed site and increase the chance of cuff implant failure. Furthermore, if sutures can not stabilize the dimension of the cuff, the edges of the cuff may overlap each other resulting in tissue damages inside the cuff.

The above disadvantages associated with prior cuff design can be addressed with the closure mechanism in this patent. This closure mechanism can provide a stable dimension for the cuff, and to ensure a smooth continuous outer surface to prevent tissue growing inwardly to the cuff lumen and to eliminate potential focal points created by using sutures. The cuff body and its closure mechanism are made of biocompatible and durable materials that can last minimum of 10 years inside a human body without significant defect. Although to increase number of closing sutures may improve the efficacy of the implantable cuff, it also increases the opportunities of having tissue growth, contaminations, and complications. This is a potential disadvantage of using cuffs in clinical settings. Decreasing the number of closing sutures may save time and simplify the procedure of implantation, but it increases the chance of cuff opening as sutures break down, and complications or failures associated with cuff opening. Reliable sutures used for implantations are relatively inexpensive to obtain and very cost effective for the end users. However, the cost of removing cuffs, procedure failures, risk of sutures break down, complications, recovery, re-evaluation, and re-implantation are fairly expensive to the health care system, insurance companies and end users. The described closure mechanism in this patent is easy to use, non-technique sensitive, not required of specialized skills, and time saving compared to using sutures.

It has been difficult to use cuffs for implantation. It requires specialized tools and surgical procedures may be challenging. To implant around a nerve or tissue of a particular locations may also be risky using a cuff. Many clinicians are reluctant to use cuffs for implantation procedures. It is delicate, time consuming, and skills required to clean out surrounding tissue and to isolate the tissue of interest. There is no simple method to open and orient the cuff during implantation procedures. The body tissue may be compressed or damaged when the cuff is not closed properly or when the surrounding tissue is not cleaned well enough. In case of complication or failures, to remove implanted cuff can be difficult due to connective tissue growth and limited access.

SUMMARY OF THE INVENTION

The cuff having a closure mechanism in this patent can improve the surgical procedure for cuff implantation. This cuff and the integral closure mechanism are shown in FIG. 1. The cuff can be opened with fingers and passed around the tissue with ease. After property enclosing the body tissue, the cuff can be closed and locked with finger pressure. When the cuff is closed, the closure mechanism seals the edges of the cuff. When the tissue of interest is not properly oriented for implantation or the surrounding tissue is not retracted well at the surgical site, the cuff will not close. Since the outer surface of the cuff is smooth and continuous when closed, the potential problem of tissue growth is minimized. When implanted cuffs are indicated for removal, the removing procedure is not complicated. The closure mechanism can be released and closed by using fingers. No specialized tools are needed to open and orient the cuff during implantation. This patent introduces the design to reduce chances of cuff implant associated complications and failure.

BRIEF DESCRIPTION OF DRAWINGS

The following drawings depict general embodiments of the implantable cuff and its closure mechanism.

FIG. 5 illustrates specific points on the implantable cuff to aid in releasing closure mechanism, opening up the cuff to enclose body tissue, and closing the cuff. FIG. 5B and FIG. 5C show the cuff opened by rotating perpendicular to the axial plane of the hinge. The hinge of the cuff body is indicated by U which runs parallel to and on the opposite side of the closure mechanism. The function of the hinge is to enable the cuff to open further and to create access to enclose specific body tissue without disturbing the dimension of the cuff.

FIG. 7 is a diagrammatic view of the semi-flexible hinge. The hinge is made of biocompatible materials relatively rigid and flexible alternating with each other forming a strip of silicones. The hinge has attachment sides to attach to the implantable cuff along its longitudinal axis. The sides of attachment on the hinge provide some degrees of rotation to the implantable cuff.

DETAILED DESCRIPTION OF THE INVENTION

An implantable cuff is used for surgical interventions in human and experimental studies in animals. This patent describes an implantable cuff with a closure mechanism. The closure mechanism provides a safe and efficient way to securely join ends of the cuff body together. This implantable cuff has several components and is fabricated as one single unit. The cuff made of biocompatible silicones cannot be dissembled, reassembled nor repaired for use.

The cuff is comprised of a tubular cuff body, a pair of closing components along the longitudinal ends of the body, a semi-flexible hinge, and a set of locking units built-in to the pair of closing components. Once the cuff is closed, the pair of closing components comes interdigitated to close the edges and the set of locking units further stabilize the closure mechanism. There is neither overlapping nor gaps on the outer surface of the cuff, and the cuff is sealed along the edge when closed.

The cuff body, the pair of closing components, locking units, and the semi-flexible hinge are made of biocompatible and durable silicone materials suitable for enclosing soft biological tissues. Each locking unit contains a silicone protrusion in one of the closing components, and a corresponding recipient housing for said silicone protrusion in the other closing components. The closing components, the cuff body, and the semi-flexible hinge made of silicones are joining together by molding or gluing to form a single unit of an implantable cuff.

Figure 1:
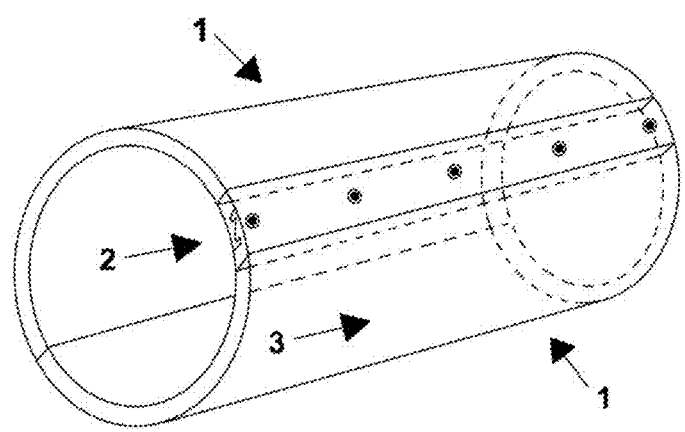
FIG. 1 is a diagrammatic view of the implantable cuff in a closed and locked position. The implantable cuff is constructed with a biocompatible and durable material. Its outer and inner surfaces are smooth without flaps, gaps nor overlapping.
Figure 2:
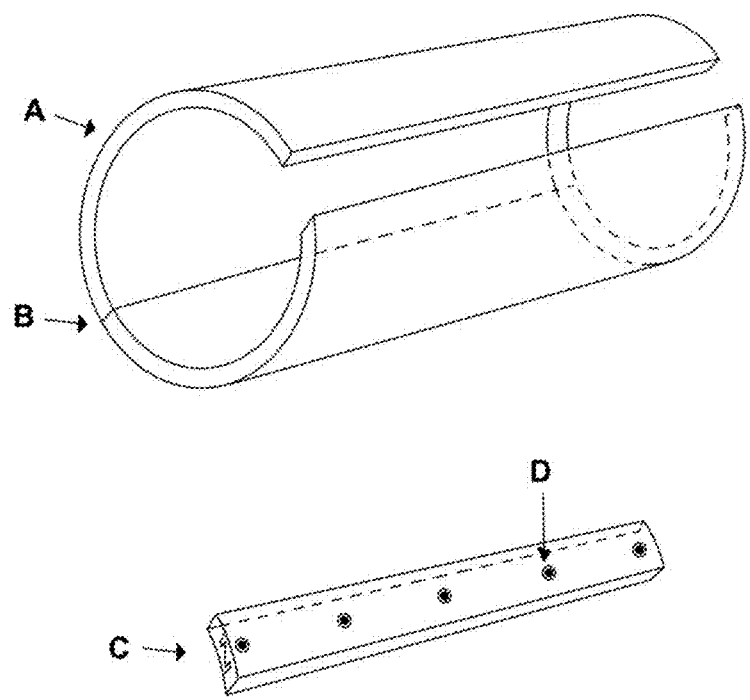
FIG. 2 illustrates two parts of an implantable cuff A tubular cuff body has a near cylindrical shape and a longitudinal hinge. The other part is the relatively rigid closure mechanism with built-in locking units.
Figure 3A:
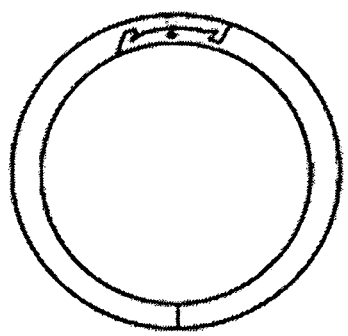
FIG. 3 shows the cross section through a plane of the cuff in FIG. 1. From this view, both closure mechanism and locking units are shown at closed and opened positions.
Figure 3B:
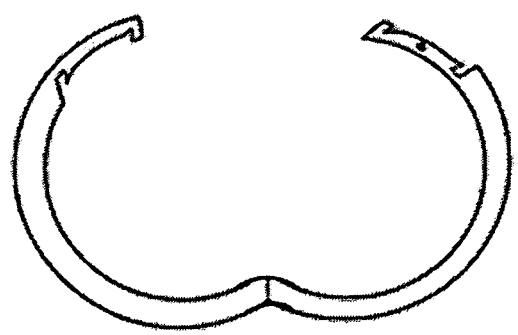
Figure 4:
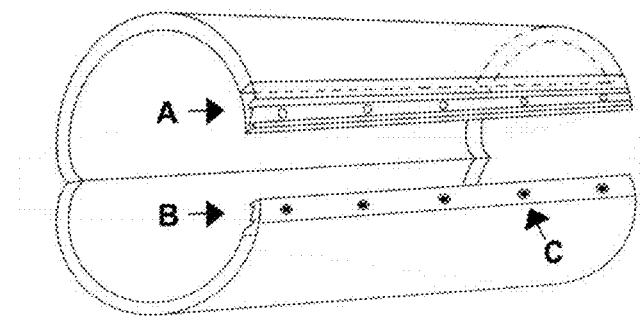
FIG. 4 is the implantable cuff at a slightly opened position. This diagram of the cuff is when the closure mechanism is just being released. The cuff is passive at this opening position without any internal or external forces exerting from or caused by its material and components. In this view, a pair of closing components A and B can be seen separately at both ends of the cuff body along the longitudinal edges. When closing components A and B are engaged to close said cuff, there are a set of locking units C enclosed within said closure mechanism.

In reference to FIG. 1, the diagrammatic design of the implantable cuff is in an ideal closed and locked position. The cuff is fabricated as one single unit. Its outer and inner surfaces are smooth without flaps, gaps nor overlapping. The tubular part of the cuff as illustrated in FIG. 2 is made of biocompatible materials with flexible or rigid physical properties that are suitable for housing components of specific applications. FIG. 2 shows a semi-flexible hinge that is embedded within the tubular cuff body and is parallel to the two longitudinal edges of the cuff. The closure mechanism as shown separately from the cuff body in FIG. 2 is constructed with a relatively rigid and durable material. FIG. 3 shows cross sectional views of the implantable cuff at its opened and closed positions. At its closed position, the implantable cuff has a near circular shape. The semi-flexible hinge is used for further opening the cuff once the closure mechanism is released. In reference to FIG. 4, the closure mechanism constitutes a pair of closing components, and a set of built-in locking units along the two edges of the cuff. When the cuff is opened, two closing components can be seen along the two longitudinal edges of the tubular cuff shown in FIG. 4. When the cuff is closed, the pair of closing components comes interdigitated with each other to close and seal the cuff along the edge. The closing components have zigzag profiles. The far ends of the profiles have the shape of a hook without pointed tips. The built-in locking units stabilize the cuff at the closed position, and prevent the cuff to re-open due to unwanted movements or forces from surrounding or enclosed tissue and applications during and after implantation. Each locking unit contains a silicone protrusion in one closing component, and a corresponding recipient housing in the other closing component. Locking units are enclosed within the closure mechanism when the cuff is closed.

The semi-flexible hinge is a part and a component of the implantable cuff A diagrammatic view of the hinge is presented in FIG. 7. Combining relatively rigid and flexible silicone in an alternating manner is to fabricate the hinge. The hinge is embedded in the cuff body. The hinge is parallel to the two long edges of the cuff body and on the opposite side of the closure mechanism when the cuff is closed. The hinge runs parallel to the closing components from one end of said tubular cuff to the other end.

The semi-flexible hinge contains silicone of different hardness values and thus the hinge is semi-flexible compared to the cuff body. The flexible cuff body flexes around a relatively rigid silicone hinge to further open the cuff Varying hardness values of silicone in the hinge allows the flexible cuff body to flex around the hinge in various degrees. The semi-flexible hinge is embedded in the cuff body. The function of the hinge is to enable the cuff to open further and to create access to enclose specific body tissue without disturbing the dimension of the cuff.

The inner surface of the cuff body may equip with pouches or pads as needed for installing clinical applications to deliver therapeutic agents such as drugs and chemicals or electrical currents to the enclosed nerves, veins, muscles, intestines, and etc. After installing applications in the pouches or pads, the inner surfaces of the cuff are prepared for additional molding process to finalize applications for use in the cuff. The inner surface of the cuff is made relatively smooth. The cuff can be used to support tissues or to promote wound healing. Electrodes can be embedded in the cuff to give electrical impulses to the surrounding tissue or to elicit certain physiological responses for specific study of interest. The implantable cuff has an embodiment having a smooth inner surface and interrupted by specific applications made of biocompatible materials such as metal electrodes. Furthermore, the cuff could be modified in other variations to record physiological signals from the enclosed tissue.

The closed implantable cuff creates a lumen shown in FIG. 1 to enclose internal body organ or tissue of tubular shape such as nerves, veins, muscles, intestines, and etc. The cuff sizes can be fabricated according to specific organ of interest and particular physiological responses to be elicited. Clinical applications of the implantable cuff with this safe and effective closure mechanism are to eliminate disadvantages of using sutures to close the cuff, to equip interfacing between internal body tissue and therapeutic agents with a reliable delivery method, preventing failure due to complications, to provide a non-technique sensitive approach and a time saving alternative for various surgical procedures.

Figure 5A:
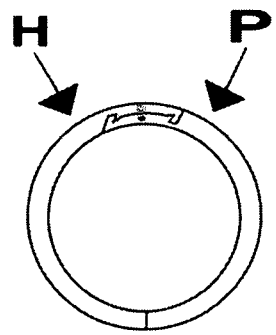
FIG. 5A and FIG. 5C show specific points to utilize for this purpose. Holding Points and Pressing Points are located on the cuff body along the longitudinal border of the closure mechanism. Holding Points are near the closing component B where the end of the hook shape pattern constitutes the outer surface of the cuff. Pressing Points are near the closing component A where the end of the hook shape pattern constitutes the inner surface of the cuff.
Figure 5B:
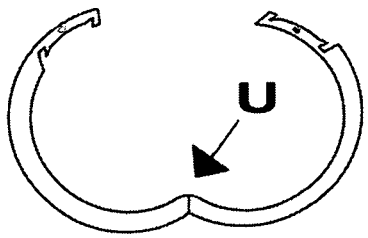
Figure 5C:
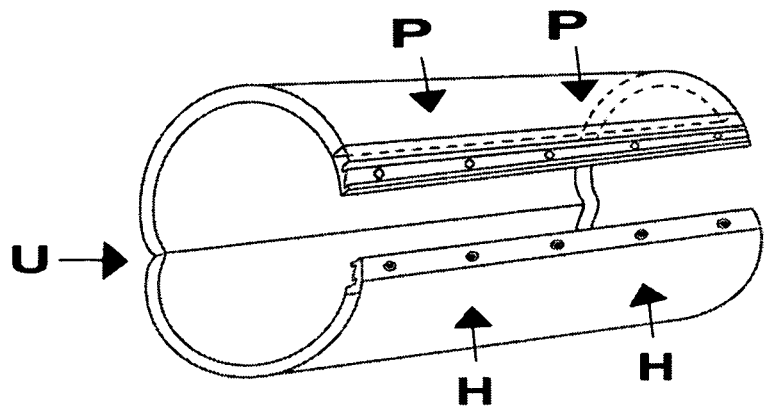
Figure 6A:
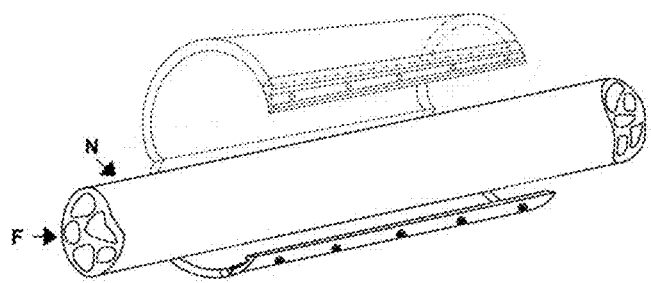
FIG. 6 shows the implantable cuff body encloses a nerve where multiple fascicles can be seen from the cross section of the nerve in FIG. 6A.
FIG. 6B is a diagram of a nerve enclosed by the cuff with the closure mechanism. The nerve is surrounded by the cuff, but the enclosed nerve is not being affixed nor tightens. The cuff is not movable nor loosens along the enclosed tissue.
Figure 6B:
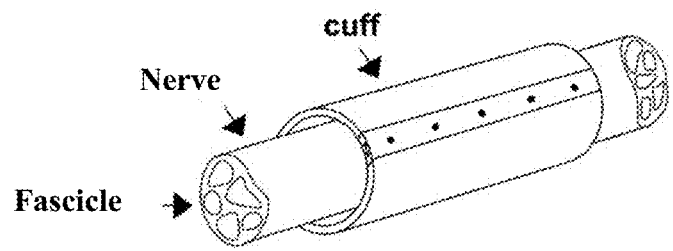

The implantable cuff has Holding Points H and Pressing Points P to use for opening and closing the cuff H and P points are shown in FIG. 5A and FIG. 5C. An instrument such as nerve or vein retractors can be useful for making access and retracting body tissue once the surrounding connective tissue is cleaned up and the body tissue is ready for enclosure. Once the tissue is retracted or the access is made, the cuff can be passed through to enclose the tissue as it is shown in FIG. 6A. Holding points and pressing points are located on the cuff body along the longitudinal border of the closure mechanism. Holding points are near the closing component B where the end of the hook shape pattern constitutes the outer surface of the cuff. Pressing points are near the closing component A where the end of the hook shape pattern constitutes the inner surface of the cuff. Holding H points and gently exerting pressure on P points rotate the cuff body and close the cuff in a locked position as shown in FIG. 6B. It is not recommended that the cuff encloses the body tissue tightly nor should the cuff be movable or loosen at the enclosure site. The implantable cuff encloses a nerve, and the enclosed nerve is not being affixed nor tighten. As indicated in FIG. 6B, the nerve is enclosed by a slightly oversized cuff without pressure nor force exerting on the enclosed nerve by the cuff.

Gently holding H points along the longitudinal border of the closure mechanism and exerting pressure onto the P points release the closure mechanism. The implantable cuff will open passively once the mechanism is released. Exerting additional pressure on P points further rotate cuff membrane perpendicular to the axial plane of the hinge, and open the cuff wider to enclose body tissue. FIG. 5B and FIG. 5C illustrate the opening cuff. The hinge is indicated by U, and it runs parallel to two longitudinal edges of the cuff and on the opposite side of the closure mechanism.

REFERENCES CITED

U.S. Patent Documents

| 5,487,756 | December 1994 | Kallesoe et al. |
| 6,461,368 B2 | October 2002 | Fogarty et al. |

The invention claimed is:

1. An implantable cuff having an integral closure mechanism comprising: a tubular cuff body of a near cylindrical shape, wherein said cuff body is made of biocompatible silicones; a closing components (A) along one long edge of said cuff body, wherein said closing components (A) constituting inner surface of said cuff is made of biocompatible silicone; a closing components (B) along the other long edge of said cuff body, wherein said closing components (B) constituting outer surface of said cuff is made of biocompatible silicone; holding points and pressing points, wherein said points located on said cuff body; a set of locking units consist of silicone protrusions and corresponding recipient housings built into said closing components; and an embedded semi-flexible hinge parallel to a longitudinal axis of said tubular cuff body.

2. The implantable cuff according to claim 1, wherein said semi-flexible hinge is configured to further open said cuff body once said closure mechanism is released; said closure mechanism consists of said closing components A and B.

3. The implantable cuff according to claim 1, wherein said semi-flexible hinge is comprised of biocompatible and durable silicone of different flexibility alternating with one another forming a strip of silicones; said hinge is embedded within said cuff body.

4. The implantable cuff according to claim 1, wherein said cuff is configured to close and seal said cuff body along its long edges; said cuff is configured to open said cuff body along said long edges; said cuff is configured to enclose an object.

5. The implantable cuff according to claim 1, wherein said semi-flexible hinge made of relatively rigid and flexible biocompatible silicone is less flexible than said cuff body; said hinge embedded in said tubular cuff body is parallel to longitudinal edges of said cuff body from one end of said tubular cuff to the other end.

6. The implantable cuff according to claim 1, wherein said closing components (A) and said closing components (B) of said closure mechanism close and seal said cuff body along longitudinal edges without gaps.

7. The implantable cuff according to claim 1, wherein said implantable cuff at close has a near circular shape in a cross-sectional view.

8. The implantable cuff according to claim 1, wherein said locking units are made of biocompatible and durable silicones; each locking unit consists of a silicone protrusion and a corresponding recipient housing built into said closing components (B) and said closing components (A), respectively.

9. The implantable cuff according to claim 1, wherein locking units are built in components in the closure mechanism to stabilize said implantable cuff.

10. The implantable cuff according to claim 1, wherein said locking units has silicone protrusions and recipient housings enclosed within said closure mechanism when said cuff is closed.

11. The implantable cuff according to claim 1, wherein said cuff body has an embodiment having a smooth inner surface interrupted by embedded metal electrodes for specific applications.

12. The implantable cuff according to claim 11, wherein said cuff is configured to use for stimulation.

13. The implantable cuff according to claim 11, wherein said cuff is configured to use for recording physiological signals.

14. The implantable cuff according to claim 1, wherein said implantable cuff once fabricated is one single unit of biocompatible silicones.

15. The implantable cuff according to claim 1, wherein said semi-flexible hinge is parallel to said closing components along longitudinal edges of said tubular cuff and on the opposite side of said closure mechanism when said tubular cuff is closed.

16. The implantable cuff according to claim 1, wherein said closing components (A) and said closing components (B) have zigzag interdigitated profiles; far ends of said profiles are hook shapes without pointed tips; said closing components are along two longitudinal edges of said tubular cuff.

17. The implantable cuff according to claim 1, wherein holding points and pressing points are located on said cuff body along longitudinal border of said closure mechanism; said holding points are near said closing component (B);

said pressing points are near said closing component (A); said points are configured to interface fingers.

18. The implantable cuff according to claim 1, wherein said closing components, said cuff body, and said hinge are joined together by molding or gluing; said cuff is fabricated as one single unit.

19. The implantable cuff according to claim 1, wherein said inner surface of said cuff contains pouches or pads for housing mechanisms according to specific therapeutic applications or clinical evaluations; said inner surface is prepared for additional molding process.

20. The implantable cuff according to claim 1, wherein said cuff is configured to enclose a nerve without pressing on said enclosed nerve; said cuff is configured not to enclose said nerve tightly; said cuff is configured to have a stable dimension at close; and said cuff is neither movable nor loosen at enclosing site.

21. The implantable cuff according to claim 1, wherein said cuff has a cylindrical continuous smooth outer surface at close; said closure mechanism close and seal said cuff without gaps; said inner and outer surfaces of said closed cuff are without flaps, gaps, nor overlapping.

\* \* \* \* \*